United States Patent
Yang et al.

(10) Patent No.: US 11,155,512 B2
(45) Date of Patent: Oct. 26, 2021

(54) METHOD AND SYSTEM FOR REFINING LONG CHAIN DICARBOXYLIC ACID

(71) Applicants: Cathay Biotech Inc., Shanghai (CN); CIBT America Inc., Newark, DE (US); Cathay (Jinxiang) Biomaterial Co., Ltd., Shandong (CN)

(72) Inventors: Chen Yang, Shanghai (CN); Bingbing Qin, Shanghai (CN); Yufeng Yang, Shanghai (CN); Kai Wang, Shanghai (CN); Xiucai Liu, Shanghai (CN)

(73) Assignees: Cathay Biotech Inc., Shanghai (CN); CIBT America Inc., Newark, DE (US); Cathay (Jinxiang) Biomaterial Co., Ltd., Shandong (CN)

( * ) Notice: Subject to any disclaimer, the term of this patent is extended or adjusted under 35 U.S.C. 154(b) by 0 days.

(21) Appl. No.: 16/887,215

(22) Filed: May 29, 2020

(65) Prior Publication Data
US 2021/0188756 A1    Jun. 24, 2021

(30) Foreign Application Priority Data
Dec. 24, 2019 (CN) .......................... 201911347657.4

(51) Int. Cl.
*C07C 51/42* (2006.01)
*C07C 51/47* (2006.01)
(Continued)

(52) U.S. Cl.
CPC ............... *C07C 51/42* (2013.01); *B01D 3/10* (2013.01); *B01D 3/12* (2013.01); *B01D 61/14* (2013.01);
(Continued)

(58) Field of Classification Search
CPC ......... C07C 51/42; C07C 51/43; C07C 51/44; C07C 51/47; C07C 57/13; C07C 55/21;
(Continued)

(56) References Cited

U.S. PATENT DOCUMENTS 4,067,779 A * 1/1978 List ...................... C07C 51/487
203/28
6,288,275 B1 * 9/2001 Turner .................... C07C 51/43
435/142

(Continued)

FOREIGN PATENT DOCUMENTS

| CN | 1351006 A | 5/2002 |
| CN | 1570124 A | 1/2005 |

(Continued)

OTHER PUBLICATIONS

JPS 5615695 (A), Mitsui Petrochemical IND, Recovery of dicarboxylic acid, English translation, 6 pages (Year: 1981).*

(Continued)

*Primary Examiner* — Yate' K Cutliff
(74) *Attorney, Agent, or Firm* — Fox Rothschild LLP

(57) ABSTRACT

The present disclosure provides a method and a system for refining long chain dicarboxylic acid, said method comprising the following steps: (1) subjecting a long chain dicarboxylic acid fermentation broth or a treated liquid therefrom to a membrane filtration, an acidification/crystallization, a solid-liquid separation and drying to give a long chain dicarboxylic acid crude product; (2) subjecting the long chain dicarboxylic acid crude product to a vacuum distillation to give the long chain dicarboxylic acid product; wherein the pressure in the vacuum distillation is ≤100 Pa. By using the refining method according to the present disclosure, the procedure is simplified, and the purity of the obtained product is high, and the disadvantages such as poor quality of the product obtained by crystallization from a (Continued)

solvent and environment pollution caused by a solvent can be overcome.

11 Claims, 1 Drawing Sheet

(51) Int. Cl.
*C07C 51/43* (2006.01)
*B01D 3/10* (2006.01)
*C07C 55/21* (2006.01)
*C07C 51/44* (2006.01)
*B01D 3/12* (2006.01)
*B01D 61/14* (2006.01)
*C12P 7/44* (2006.01)

(52) U.S. Cl.
CPC .............. *C07C 51/43* (2013.01); *C07C 51/44* (2013.01); *C07C 55/21* (2013.01); *C07C 51/47* (2013.01); *C12P 7/44* (2013.01)

(58) Field of Classification Search
CPC .. B01D 61/14; B01D 1/10; B01D 1/12; C12P 7/44
See application file for complete search history.

(56) References Cited

U.S. PATENT DOCUMENTS

| | | | | |
|---|---|---|---|---|
| 9,272,976 B2 * | 3/2016 | Schulze | ................. | C07C 51/47 |
| 9,517,996 B2 * | 12/2016 | Laplaza | ................. | C07C 55/20 |
| 2013/0096343 A1 * | 4/2013 | Tietz | ....................... | C07C 51/47 |
| | | | | 562/593 |

FOREIGN PATENT DOCUMENTS

| | | | | | |
|---|---|---|---|---|---|
| CN | 101177650 A | | 5/2008 | | |
| CN | 102503800 B | | 6/2014 | | |
| CN | 109516913 A | | 3/2019 | | |
| CN | 110272341 A | | 9/2019 | | |
| GB | 2203425 A | * | 10/1988 | ............. | C07C 57/13 |
| JP | S50149616 A | | 11/1975 | | |
| JP | S 5615695 A | * | 2/1981 | ................ | C12P 7/44 |
| JP | S63258830 A | | 10/1988 | | |

OTHER PUBLICATIONS

Extended European Search Report dated Nov. 10, 2020 in related EP Application No. 20178389.1; 6 pgs.

* cited by examiner

METHOD AND SYSTEM FOR REFINING LONG CHAIN DICARBOXYLIC ACID

CROSS REFERENCE

This application is based upon and claims priority to Chinese Patent Application No. 201911347657.4, filed on Dec. 24, 2019, the entire contents thereof are incorporated herein by reference.

TECHNICAL FIELD

The present disclosure relates to long chain dicarboxylic acid, specifically to a method and a system for refining long chain dicarboxylic acid produced by biological fermentation.

BACKGROUND ART

Long chain dicarboxylic acids (LCDAs, abbreviated as DCn, n=9-18) are a group of important organic intermediates, which are widely used in fields such as chemical engineering, light industry, agricultural chemicals, medicine and new materials. Currently, the most conventional method for preparing long chain dicarboxylic acid is biological fermentation of long carbon chain alkane, fatty acid, fatty acid ester or fatty acid salt in the presence of a specific strain. The technologies for extracting and purifying long chain dicarboxylic acid also affect the cost of the final industrially produced dicarboxylic acid. Therefore, the development of a simple and highly efficient technology for extracting and purifying dicarboxylic acid will promote the application of the fermentation technology.

Currently, long chain dicarboxylic acid is normally purified by recrystallization with an organic solvent. CN102503800A discloses a method for refining long chain dicarboxylic acid, in which the long chain dicarboxylic acid crude product is recrystallized with an alcohol or acetone as the solvent to give refined long chain dicarboxylic acid. Although the yield of refining may be improved by diluted solvent, refining long chain dicarboxylic acid with an alcohol as the solvent has a disadvantage that the dicarboxylic acid and ethanol undergo esterification at an elevated temperature, producing new products during the refining process, which affects the purity of the product.

In addition, the recrystallization treatment mainly utilizes the difference in the solubility to remove impurities. However, some impurities may have similar solubility with the long chain dicarboxylic acid, which cannot be completely removed even with repeated recrystallization. The product obtained by crystallization from an organic solvent has a problem of residual solvent.

SUMMARY OF INVENTION

The present disclosure provides a method for refining long chain dicarboxylic acid, comprising the following steps:

(1) subjecting a long chain dicarboxylic acid fermentation broth or a treated liquid therefrom to a membrane filtration, an acidification/crystallization, a solid-liquid separation and drying to give a long chain dicarboxylic acid crude product;

(2) subjecting the long chain dicarboxylic acid crude product to a vacuum distillation to give the long chain dicarboxylic acid product;

wherein the pressure in the vacuum distillation is ≤100 Pa.

The present disclosure further provides a long chain dicarboxylic acid which is obtained by the above method.

The present disclosure further provides a long chain dicarboxylic acid product, having a purity of equal to or more than 97.5 wt %, preferably equal to or more than 98 wt %, more preferably equal to or more than 98.5 wt %; a total acid content of equal to or more than 98.5 wt %, preferably equal to or more than 99 wt %; an ash content of equal to or less than 50 ppm, preferably equal to or less than 30 ppm; a nitrogen content of equal to or less than 50 ppm; an iron content of equal to or less than 2 ppm; a light transmittance of equal to or more than 92%, preferably equal to or more than 95%, more preferably equal to or more than 97%, more preferably equal to or more than 99%.

The present disclosure further provides a system for refining long chain dicarboxylic acid, comprising:

a membrane filtration unit, for a membrane filtration of a long chain dicarboxylic acid fermentation broth or a treated liquid therefrom;

an acidification/crystallization unit, for an acidification/crystallization of a filtrate obtained after the membrane filtration to give a solid-liquid mixture;

a separation unit, for a solid-liquid separation of the solid-liquid mixture;

a drying unit, for drying the solid separated by the separation unit to give a long chain dicarboxylic acid crude product; and a vacuum distillation unit, for a distillation of the long chain dicarboxylic acid crude product to give a long chain dicarboxylic acid product.

By using the method for refining long chain dicarboxylic acid according to one embodiment of the present disclosure, the procedure is simplified, and the purity of the obtained product is high, and the disadvantages such as high requirements on equipments by crystallization from the solvent, need of a solvent recovery system, test of solvent safety, environment pollution caused by the solvent can be overcome.

SPECIFIC EMBODIMENTS

Figure 1:
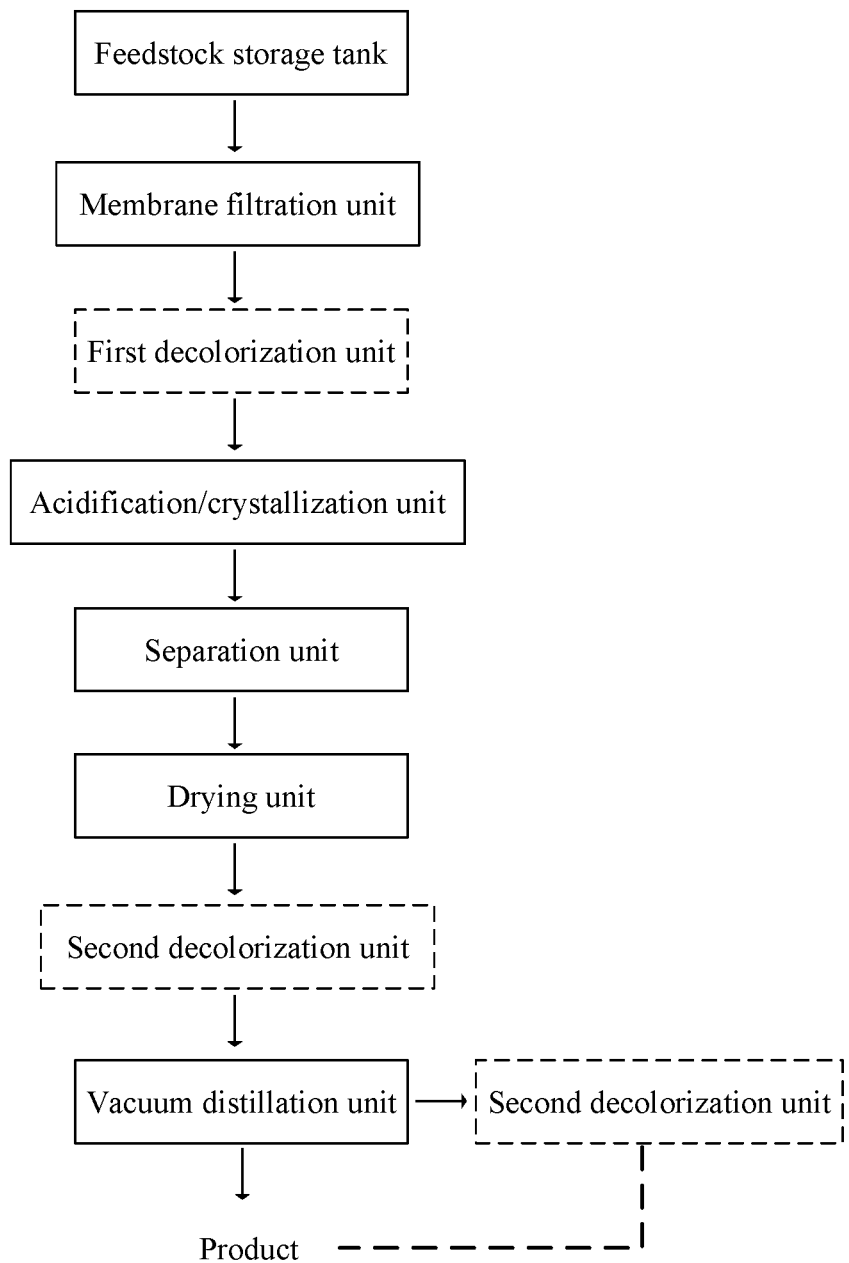
FIG. 1 shows a scheme of the system for refining long chain dicarboxylic acid according to one embodiment of the present disclosure.

Typical embodiments reflecting the features and advantages of the present disclosure will be detailed in the description below. It shall be understood that the present disclosure may have various changes in different embodiments, without departing from the scope of the present disclosure, and the description and figures therein are illustrative in nature, not limiting the present disclosure. In the description, the terms "first", "second", etc., are used to distinguish a variety of processes or products with the same names, not limiting thereto.

An embodiment of the present disclosure provides a method for refining long chain dicarboxylic acid from a long chain dicarboxylic acid fermentation broth or a treated liquid therefrom, said method comprising:

(1) subjecting the long chain dicarboxylic acid fermentation broth or a treated liquid therefrom to a membrane filtration, an acidification/crystallization, a solid-liquid separation and drying to give a long chain dicarboxylic acid crude product;

(2) subjecting the long chain dicarboxylic acid crude product to a vacuum distillation to give the long chain dicarboxylic acid product;

wherein the pressure in the vacuum distillation is ≤100 Pa, preferably ≤50 Pa.

In the present disclosure, the long chain dicarboxylic acid fermentation broth may be a fermentation broth obtained by microbial fermentation using alkane, fatty acid or a derivative thereof as the substrate; and the microorganism converts the terminal methyl group of alkane, fatty acid or fatty acid derivative to carboxyl group through oxidation, so as to produce a long chain dicarboxylic acid.

In an embodiment, the treated liquid from the long chain dicarboxylic acid fermentation broth is a liquid obtained after removing one or more components other than the long chain dicarboxylic acid salt from the fermentation broth or reducing the contents thereof. For example, the fermentation broth is subjected to centrifugation or membrane filtration to separate out the bacterial body and the residual substrate to give the treated liquid.

In an embodiment, the long chain dicarboxylic acid is a $C_9$-$C_{18}$ dicarboxylic acid.

In an embodiment, the long chain dicarboxylic acid is a linear saturated or non-saturated dicarboxylic acid; and has carboxyl groups at both ends.

In an embodiment, the long chain dicarboxylic acid may be one or more of azelaic acid, sebacic acid, undecandioic acid, dodecanedioic acid, tridecandioic acid, tetradecandioic acid, pentadecandioic acid, hexadecandioic acid, heptadecandioic acid, octadecandioic acid and 9-octadecene diacid.

In an embodiment, before the membrane filtration, a base may be added to the fermentation broth or the treated liquid therefrom to dissolve the long chain dicarboxylic acid.

In an embodiment, the pH of the fermentation broth or the treated liquid therefrom may be adjusted to 6-12, preferably 8-11, such as 8.2, 8.5, 8.8, 9.0, 9.2, 9.5, 9.8, 10.0, 10.2, 10.5, 10.8 or 11.5. The base added may be sodium hydroxide or potassium hydroxide.

In an embodiment, before the membrane filtration, the fermentation broth or the treated liquid therefrom may be heated to 60-100° C., such as 62° C., 65° C., 68° C., 70° C., 72° C., 75° C., 78° C., 80° C., 82° C., 85° C., 88° C., 90° C., 92° C., 95° C. or 98° C.

In an embodiment, the membrane filtration includes an ultrafiltration membrane filtration and/or a microfiltration membrane filtration.

In an embodiment, the temperature for the microfiltration membrane filtration is 30-100° C., preferably 50-100° C., more preferably 60-100° C., such as 35° C., 40° C., 45° C., 50° C., 55° C., 60° C., 62° C., 65° C., 68° C., 70° C., 72° C., 75° C., 78° C., 80° C., 82° C., 84° C., 85° C., 86° C., 88° C., 90° C., 92° C., 94° C., 95° C., 96° C. or 98° C.

In an embodiment, the pore size of the microfiltration membrane may be 0.01-1 μm, preferably 0.01-0.2 μm, more preferably 0.02-0.1 μm, such as 0.03 μm, 0.05 μm, 0.08 μm, 0.1 μm, 0.15 μm or 0.5 μm.

In an embodiment, the temperature for the ultrafiltration membrane filtration is 20-100° C., preferably 20-45° C., more preferably 30-40° C., such as 25° C., 30° C., 32° C., 34° C., 35° C., 36° C. or 38° C.

In an embodiment, the cut-off molecular weight of the ultrafiltration membrane may be 1000-200000 Da, preferably 1000-30000 Da, more preferably 1000-10000 Da, such as 1500 Da, 2000 Da, 3000 Da, 4000 Da, 5000 Da, 6000 Da, 8000 Da, 10000 Da, 15000 Da, 20000 Da or 25000 Da.

In an embodiment, the ultrafiltration membrane may be polypropylene membrane, a polysulfone membrane, a polyethersulfone membrane, or an inorganic ultrafiltration membrane, such as a ceramic membrane.

In an embodiment, the membrane filtration includes a microfiltration membrane filtration and an ultrafiltration membrane filtration, in which the fermentation broth or the treated liquid therefrom is first subjected to the microfiltration membrane filtration, and then the filtrate is subjected to the ultrafiltration membrane filtration.

In an embodiment, the fermentation broth or the treated liquid therefrom is subjected to the microfiltration membrane filtration at 60-100° C., and the resulted filtrate is cooled to 20-45° C., and then subjected to the ultrafiltration membrane filtration.

In step (1) of an embodiment, the filtrate after the membrane filtration is subjected to a decolorization treatment and then to an acidification/crystallization.

In step (1) of an embodiment, the temperature for the decolorization treatment may be 50-100° C., preferably 60-100° C., more preferably 60-80° C., such as 62° C., 65° C., 68° C., 70° C., 72° C., 75° C., 78° C., 80° C., 85° C., 88° C., 90° C. or 95° C.

In step (1) of an embodiment, the duration for the decolorization treatment may be 10-180 min, preferably 15-120 min, such as 20 min, 30 min, 40 min, 60 min, 70 min, 80 min, 90 min, 100 min, 110 min, 130 min, 150 min or 170 min.

In step (1) of an embodiment, the decolorant used for the decolorization treatment may be activated carbon fiber, activated carbon particle or activated carbon powder, and the amount of the decolorant used may be 0.05-5 wt %, such as 1 wt %, 1.5 wt %, 2 wt %, 2.5 wt %, 3 wt %, 3.5 wt % or 4 wt %, relative to the mass of the liquid to be decolorized.

In an embodiment, the acidification/crystallization comprises adjusting the pH of the filtrate to 2-5.5 for the crystallization to occur.

In an embodiment, the acidification/crystallization process comprises adjusting the pH of the filtrate obtained by the membrane filtration or the clear liquid obtained by the decolorization treatment to 2-4.5, preferably 2-4, more preferably 2.5-4, more preferably 2.5-3.7, such as 2.2, 2.5, 2.8, 3.0, 3.2, 3.5, 3.7, 3.8, 4.0, 4.2, 4.3 or 4.5, to allow the long chain dicarboxylic acid to crystallize and precipitate.

In an embodiment, the pH of the filtrate obtained by the membrane filtration or the clear liquid obtained by the decolorization treatment may be adjusted by adding an acid thereto, which may be an inorganic acid and/or an organic acid. The inorganic acid added may be hydrochloric acid and/or sulfuric acid.

In an embodiment, step (1) comprises:

heating the long chain dicarboxylic acid fermentation broth or the treated liquid therefrom to 30-100° C., adjusting its pH to 8-11, then subjecting it to a membrane filtration at 20-100° C., to give a filtrate;

subjecting the filtrate to a decolorization treatment at 50-100° C. to give a clear liquid; and adjusting the pH of the clear liquid to 2-4.5 to allow crystals to precipitate, which are filtered and dried to give the long chain dicarboxylic acid crude product.

In an embodiment, step (2) comprises: subjecting the long chain dicarboxylic acid crude product to a vacuum distillation, and collecting the fraction to give the long chain dicarboxylic acid product.

In an embodiment, the pressure for the vacuum distillation may be 1-100 Pa, preferably 1-50 Pa, such as 3 Pa, 5 Pa, 6 Pa, 10 Pa, 15 Pa, 20 Pa, 25 Pa, 30 Pa, 50 Pa, 60 Pa or 80 Pa.

In an embodiment, the vacuum distillation includes a molecular distillation and a high vacuum distillation.

In an embodiment, the pressure in the main evaporator for the molecular distillation may be 0.1-30 Pa, preferably 0.1-15 Pa, such as 1 Pa, 2 Pa, 5 Pa, 6 Pa, 8 Pa, 10 Pa, 12 Pa, 16 Pa, 18 Pa, 20 Pa or 25 Pa.

In an embodiment, the temperature of the evaporation surface of the main evaporator for the molecular distillation is 130-250° C., preferably 160-230° C., such as 140° C., 150° C., 160° C., 180° C., 200° C., 210° C., 220° C. or 240° C.

In an embodiment, the temperature of the condensation surface of the main evaporator for the molecular distillation is 130-160° C., preferably 130-150° C., such as 135° C., 140° C., 145° C., 150° C. or 155° C.

In an embodiment, the inlet temperature for the molecular distillation is 130-160° C., preferably 135-150° C., such as 130° C., 135° C., 140° C., 145° C., 150° C. or 155° C.

In an embodiment, the number of theoretical plates of the rectifying column used in the high vacuum distillation may be 8-24, preferably 12-20, such as 10, 12, 18 or 24. Preferably, a packed column is used, and the packing may be that commonly used in the art, such as corrugated wire mesh packing.

In an embodiment, the overhead pressure of the rectifying column used in the high vacuum distillation may be 1-100 Pa, preferably 1-50 Pa, such as 20 Pa, 30 Pa, 60 Pa, 70 Pa or 80 Pa.

In an embodiment, the overhead temperature of the rectifying column used in the high vacuum distillation may be 160-250° C., preferably 180-240° C., such as 170° C., 185° C., 190° C., 195° C., 200° C., 210° C., 220° C., 225° C., 228° C., 230° C., 232° C., 235° C., 238° C., 240° C. or 245° C.

In an embodiment, the bottom temperature of the rectifying column used in the high vacuum distillation may be 180-270° C., such as 190° C., 200° C., 210° C., 220° C., 230° C., 240° C., 243° C., 245° C., 248° C., 250° C., 255° C., 260° C. or 265° C.

In an embodiment, the reflux ratio in the high vacuum distillation may be (1-10):1, preferably (6-10):1, such as 1:1, 2:1, 5:1, 6:1, 8:1 or 10:1.

In step (2) of an embodiment, the decolorization treatment may be carried out to the long chain dicarboxylic acid crude product before the vacuum distillation, or to the product obtained after the vacuum distillation.

In step (2) of an embodiment, the decolorization treatment may be a solution decolorization or a melt decolorization.

In an embodiment, the decolorant used for the decolorization treatment may be activated carbon.

In an embodiment, the melt decolorization refers to directly contacting the long chain dicarboxylic acid crude product or the fraction to be decolorized obtained by the vacuum distillation with the decolorant for carrying out the decolorization. For example, the long chain dicarboxylic acid crude product or the fraction obtained by the vacuum distillation is heated and melted, and passed over the decolorant in the melt form.

Both subjecting the long chain dicarboxylic acid crude product to the melt decolorization and then to the vacuum distillation and subjecting the fraction obtained by the vacuum distillation to the melt decolorization can reduce the energy consumption for heating and simplify the process.

In an embodiment, the temperature for the melt decolorization may be 130-180° C., preferably 130-150° C., such as 135° C., 140° C., 145° C., 150° C., 155° C., 160° C., 165° C., 170° C. or 175° C.

In an embodiment, the amount of the activated carbon used for the melt decolorization is 3-50 wt %, preferably 5-25 wt %, such as 5 wt %, 10 wt %, 15 wt %, 20 wt %, 25 wt %, 30 wt %, 35 wt %, 40 wt % or 45 wt % of the mass of the long chain dicarboxylic acid crude product or of the mass of the fraction obtained by vacuum distillation.

In an embodiment, after the melt decolorization is completed, the residual activated carbon may be removed by filtration. By the melt decolorization, the substance to be decolorized is decolorized and purified, while introduction of further impurities is avoided.

In an embodiment, the activated carbon used for the decolorization treatment may be one or more of powdered activated carbon, activated carbon fiber, activated carbon particle, activated carbon column.

According to the requirements on the product quality by the customer or by the market, the product obtained by the refining method according to the present disclosure may be further refined to further improve the product quality.

By using the refining method according to an embodiment of the present disclosure, the procedure is simplified, and the disadvantages such as poor quality of the product obtained by crystallization from a solvent and environment pollution caused by a solvent can be overcome.

The refining method according to an embodiment the present disclosure is suitable for purifying long chain dicarboxylic acid produced by biological fermentation. By using the combination of membrane filtration and distillation, especially the combination of a ceramic membrane filtration, an ultrafiltration membrane filtration and a molecular distillation or a high vacuum distillation, no organic solvent is necessary, and the resulted product has a high purity, white color, low ash content, low metal content and low nitrogen content.

An embodiment of the present disclosure provides a long chain dicarboxylic acid obtained by the above refining method.

As shown in FIG. 1, an embodiment of the present disclosure provides a system for refining long chain dicarboxylic acid which realizes the above refining method, comprises a membrane filtration unit, an acidification/crystallization unit, a separation unit, a drying unit and a vacuum distillation unit, which are sequentially configured.

In an embodiment, the refining system comprises a feedstock storage tank, which may be connected to the membrane filtration unit, for holding the long chain dicarboxylic acid fermentation broth or the treated liquid therefrom.

In an embodiment, the membrane filtration unit is used for the membrane filtration of the long chain dicarboxylic acid fermentation broth or the treated liquid therefrom. A filtration membrane, such as a microfiltration membrane and/or an ultrafiltration membrane, may be disposed in the membrane filtration unit.

In an embodiment, the pore size of the microfiltration membrane may be 0.01-1 μm, preferably 0.02-0.2 μm, more preferably 0.02-0.1 μm, such as 0.03 μm, 0.05 μm, 0.08 μm, 0.1 μm, 0.15 μm or 0.5 μm.

In an embodiment, the cut-off molecular weight of the ultrafiltration membrane may be 1000-200000 Da, preferably 1000-30000 Da, more preferably 1000-10000 Da, such as 1500 Da, 2000 Da, 3000 Da, 4000 Da, 5000 Da, 6000 Da, 8000 Da, 10000 Da, 15000 Da, 20000 Da or 25000 Da.

In an embodiment, the ultrafiltration membrane may be polypropylene membrane, polysulfone membrane, polyethersulfone membrane, or an inorganic ultrafiltration membrane, such as a ceramic membrane.

In an embodiment, the refining system comprises a heating device for heating the feedstock storage tank, so that the long chain dicarboxylic acid fermentation broth or the treated liquid therefrom is subjected to the membrane filtration at a certain temperature, such as 50-100° C.

In an embodiment, the long chain dicarboxylic acid fermentation broth is subjected to a membrane filtration in the membrane filtration unit to give a filtrate. An acidification/crystallization unit is used for an acidification/crystallization of the filtrate.

In an embodiment, the acidification/crystallization unit comprises an acidification tank, in which the filtrate undergoes the acidification/crystallization to give a solid-liquid mixture.

In an embodiment, a first decolorization unit may be disposed between the membrane filtration unit and the acidification/crystallization unit, so that the filtrate is subjected to the decolorization treatment and then to the acidification/crystallization.

In an embodiment, the first decolorization unit may comprise a decolorization tank and a filter. The decolorization tank is used for mixing the liquid to be decolorized and the solid decolorant for carrying out the decolorization. After the decolorization is completed, the solid decolorant may be filtered out by the filter which may be a plate-and-frame filter.

In an embodiment, the first decolorization unit comprises a heating device for heating the decolorization tank, so that the decolorization treatment is carried out at a certain temperature (e.g., 50-100° C.).

In an embodiment, the separation unit is used for a solid-liquid separation of the solid-liquid mixture obtained in the acidification/crystallization unit.

In an embodiment, the separation unit may comprise a filtration device or a centrifuge.

In an embodiment, the drying unit comprises a heating device for heating and drying the solid obtained by the separation unit to give the long chain dicarboxylic acid crude product.

In an embodiment, a vacuum distillation unit is used to distill and separate the dried long chain dicarboxylic acid crude product to give the long chain dicarboxylic acid product.

In an embodiment, the vacuum distillation unit comprises a heating device to bring the long chain dicarboxylic acid crude product to the melting state.

In an embodiment, the vacuum distillation unit comprises a distillation device for carrying out the vacuum distillation process.

In an embodiment, the distillation device comprises a molecular distillation device for carrying out a molecular distillation.

In another embodiment, the distillation device comprises a rectifying column for carrying out a high vacuum distillation.

In an embodiment, the number of theoretical plates in the rectifying column may be 8-24, preferably 12-20, such as 10, 12, 18 or 24.

In an embodiment, the refining system comprises a second decolorization unit.

In an embodiment, the second decolorization unit may comprise a decolorization tank and a filter. The decolorization tank is used for mixing the liquid to be decolorized and the solid decolorant for carrying out the decolorization. After the decolorization is completed, the solid decolorant may be filtered out by the filter which may be a plate-and-frame filter.

In an embodiment, the long chain dicarboxylic acid crude product or the fraction obtained by the vacuum distillation is directly contacted with the decolorant in the second decolorization unit for carrying out a decolorization. For example, the long chain dicarboxylic acid crude product or the fraction obtained by the vacuum distillation flows over the decolorant in the second decolorization unit in a melting state.

In an embodiment, the second decolorization unit comprises a heating device for heating the decolorization tank, so that the decolorization treatment is carried out at a certain temperature (e.g., 130-180° C.).

In an embodiment, the second decolorization unit is disposed between the drying unit and the vacuum distillation unit, so that a decolorization treatment of the long chain dicarboxylic acid crude product is carried out before the vacuum distillation. Alternatively, the second decolorization unit is disposed after the vacuum distillation unit, so that the product after the vacuum distillation is subjected to a decolorization treatment.

In another embodiment, the long chain dicarboxylic acid crude product or the fraction obtained by the vacuum distillation is heated and melted, and then decolorized with the decolorant. After the decolorization, the residual decolorant may be removed by filtration to give the second long chain dicarboxylic acid crude product or the long chain dicarboxylic acid product.

In the present disclosure, the acidification tank, the decolorization tank, the dissolution tank and the heating device may be known equipments.

In the following, the method for refining long chain dicarboxylic acid according to an embodiment of the present disclosure is described in detail by way of specific examples, in which the raw materials used, without otherwise specified, are all commercially available, and the test methods are as follows:

1. Gas chromatographic test of long chain dicarboxylic acid

A standard long chain dicarboxylic acid sample was used as the control, and GB5413.27-2010 "Determination of fatty acids in foods for infants and young children, milk and milk products" is referred to.

2. Ash content test

A test sample was calcined in a crucible, then in a muffle furnace at 700-800° C. for 2 hours. After cooling to constant weight, the weight was measured, and the weight percentage was calculated.

3. Total nitrogen test

Kjeldahl determination was used.

4. Light transmittance test

Substances with different colors have different light transmittances at a certain wavelength. Based on this, the color of the dicarboxylic acid product is represented by the light transmittances of a 25 wt. % solution of the long chain dicarboxylic acid sample in dimethyl sulfoxide at 440 nm.

5. Fe content test

Fe content was determined by spectroscopy referring to GB/T3049-2006.

Example 1. DC12, Microfiltration Membrane Filtration+Molecular Distillation

Following the fermentation method disclosed in Example 4 of CN1570124A, a dodecanedioic acid (DC12) fermentation broth was obtained.

The fermentation broth was heated to 85° C., followed by adding a base to adjust the pH to 8.2. The fermentation broth was filtered at 85° C. with a ceramic microfiltration membrane having a pore size of 0.05 μm to remove the bacterial body to give a filtrate.

The filtrate was decolorized with 3 wt % activated carbon at 85° C. for 40 min, and filtered with a plate-and-frame filter to give a clear liquid, which was adjusted with sulfuric acid to pH 2.8 to carry out an acidification/crystallization, filtered and dried to give the DC12 crude product.

The DC12 crude product was purified by a molecular distillation, in which the pressure in the main evaporator of the molecular distillation device was 18 Pa, the temperature of the evaporation surface of the main evaporator was 180° C., the temperature of the condensation surface of the main evaporator was 140° C., and the feedstock inlet temperature was 130° C. The fraction was collected to give the DC12 product.

Example 2. DC12, Microfiltration Membrane Filtration+High Vacuum Distillation

Following the fermentation method disclosed in Example 4 of CN1570124A, a dodecanedioic acid fermentation broth was obtained.

The fermentation broth was heated to 85° C., followed by adding a base to adjust the pH to 8.2. The fermentation broth was filtered at 85° C. with a ceramic microfiltration membrane having a pore size of 0.05 μm to remove the bacterial body to give a filtrate.

The filtrate was decolorized with 3 wt % activated carbon at 85° C. for 20 min, and filtered with a plate-and-frame filter to give a clear liquid, which was adjusted with sulfuric acid to pH 2.8 to carry out an acidification/crystallization, filtered and dried to give the DC12 crude product.

The DC12 crude product was purified by a high vacuum distillation, in which the rectifying column had a plate number of 12, an overhead pressure of 60 Pa, an overhead temperature of 238° C., a bottom temperature of 250° C., and a reflux ratio of 5:1. The fraction was collected and cooled to give the DC12 product.

Example 3. DC16, Microfiltration Membrane Filtration+Ultrafiltration Membrane Filtration+Molecular Distillation Following the fermentation method disclosed in Example 8 of CN1570124A, a hexadecandioic acid (DC16) fermentation broth was obtained.

The fermentation broth was heated to 90° C., followed by adding a base to adjust the pH to 8.5. The fermentation broth was filtered at 90° C. with a ceramic microfiltration membrane having a pore size of 0.05 μm to remove the bacterial body, then cooled to 30° C., and filtered at 30° C. with an ultrafiltration membrane having a cut-off molecular weight of 5000 Da, to give a filtrate.

The filtrate was decolorized with 2.5 wt % activated carbon at 85° C. for 20 min, and filtered with a plate-and-frame filter to give a clear liquid, which was adjusted with hydrochloric acid to pH 3.0 to carry out an acidification/crystallization, filtered and dried to give the DC16 crude product.

The DC16 crude product was purified by a molecular distillation, in which the pressure in the main evaporator of the molecular distillation device was 6 Pa, the temperature of the evaporation surface of the main evaporator was 200° C., the temperature of the condensation surface of the main evaporator was 150° C., and the feedstock inlet temperature was 140° C. The fraction was collected and cooled to give the DC16 product.

Example 4-1. DC12, Microfiltration Membrane Filtration+Ultrafiltration Membrane Filtration+Molecular Distillation Following the fermentation method disclosed in Example 4 of CN1570124A, a dodecanedioic acid fermentation broth was obtained.

The DC12 fermentation broth was heated to 90° C., followed by adding a base to adjust the pH to 8.5. The fermentation broth was filtered at 90° C. with a ceramic microfiltration membrane having a pore size of 0.05 μm to remove the bacterial body, then cooled to 35° C., and filtered at 35° C. with an ultrafiltration membrane having a cut-off molecular weight of 5000 Da, to give a filtrate.

The filtrate was decolorized with 2.5 wt % activated carbon at 85° C. for 20 min, and filtered with a plate-and-frame filter to give a clear liquid, which was adjusted with sulfuric acid to pH 3.0 to carry out an acidification/crystallization, filtered and dried to give the DC12 crude product.

The DC12 crude product was purified by a molecular distillation, in which the pressure in the main evaporator of the molecular distillation device was 5 Pa, the temperature of the evaporation surface of the main evaporator was 180° C., the temperature of the condensation surface of the main evaporator was 140° C., and the feedstock inlet temperature was 130° C. The fraction was collected and cooled to give the DC12 product.

Example 4-2. DC12, Microfiltration Membrane Filtration+Ultrafiltration Membrane Filtration+Molecular Distillation Following the fermentation method disclosed in Example 4 of CN1570124A, a dodecanedioic acid fermentation broth was obtained.

The DC12 fermentation broth was heated to 90° C., followed by adding a base to adjust the pH to 8.5. The fermentation broth was filtered at 90° C. with a ceramic microfiltration membrane having a pore size of 0.15 μm to remove the bacterial body, then cooled to 35° C., and filtered at 35° C. with an ultrafiltration membrane having a cut-off molecular weight of 15000 Da, to give a filtrate.

The filtrate was decolorized with 2.5 wt % activated carbon at 85° C. for 20 min, and filtered with a plate-and-frame filter to give a clear liquid, which was adjusted with sulfuric acid to pH 4 to carry out an acidification/crystallization, filtered and dried to give the DC12 crude product.

The DC12 crude product was purified by a molecular distillation, in which the pressure in the main evaporator of the molecular distillation device was 8 Pa, the temperature of the evaporation surface of the main evaporator was 180° C., the temperature of the condensation surface of the main evaporator was 140° C., and the feedstock inlet temperature was 130° C. The fraction was collected and cooled to give the DC12 product.

Example 4-3. DC12, Microfiltration Membrane Filtration+Ultrafiltration Membrane Filtration+Molecular Distillation Following the fermentation method disclosed in Example 4 of CN1570124A, a dodecanedioic acid fermentation broth was obtained.

The DC12 fermentation broth was heated to 90° C., followed by adding a base to adjust the pH to 8.5. The fermentation broth was filtered at 90° C. with a ceramic microfiltration membrane having a pore size of 0.05 µm to remove the bacterial body, then cooled to 35° C., and filtered at 35° C. with an ultrafiltration membrane having a cut-off molecular weight of 15000 Da, to give a filtrate.

The filtrate was decolorized with 2.5 wt % activated carbon at 85° C. for 20 min, and filtered with a plate-and-frame filter to give a clear liquid, which was adjusted with sulfuric acid to pH 4.5 to carry out an acidification/crystallization, filtered and dried to give the DC12 crude product.

The DC12 crude product was purified by a molecular distillation, in which the pressure in the main evaporator of the molecular distillation device was 18 Pa, the temperature of the evaporation surface of the main evaporator was 150° C., the temperature of the condensation surface of the main evaporator was 130° C., and the feedstock inlet temperature was 130° C. The fraction was collected and cooled to give the DC12 product.

Example 5-1. DC12, Microfiltration Membrane Filtration+Ultrafiltration Membrane Filtration+High Vacuum Distillation Following the fermentation method disclosed in Example 4 of CN1570124A, a dodecanedioic acid fermentation broth was obtained.

The DC12 fermentation broth was heated to 90° C., followed by adding a base to adjust the pH to 8.5. The fermentation broth was filtered at 90° C. with a ceramic microfiltration membrane having a pore size of 0.05 µm to remove the bacterial body, then cooled to 35° C., and filtered at 35° C. with an ultrafiltration membrane having a cut-off molecular weight of 5000 Da, to give a filtrate.

The filtrate was decolorized with 2.5 wt % activated carbon at 85° C. for 20 min, and filtered with a plate-and-frame filter to give a clear liquid, which was adjusted with sulfuric acid to pH 3.0 to carry out an acidification/crystallization, filtered and dried to give the DC12 crude product.

The DC12 crude product was purified by a high vacuum distillation, in which the rectifying column had a plate number of 10, an overhead pressure of 30 Pa, an overhead temperature of 230° C., a bottom temperature of 243° C., and a reflux ratio of 5:1. The fraction was collected and cooled to give the DC12 product.

Example 5-2. DC12, Microfiltration Membrane Filtration+Ultrafiltration Membrane Filtration+High Vacuum Distillation Following the fermentation method disclosed in Example 4 of CN1570124A, a dodecanedioic acid fermentation broth was obtained.

The DC12 fermentation broth was heated to 90° C., followed by adding a base to adjust the pH to 8.5. The fermentation broth was filtered at 90° C. with a ceramic microfiltration membrane having a pore size of 0.15 µm to remove the bacterial body, then cooled to 35° C., and filtered at 35° C. with an ultrafiltration membrane having a cut-off molecular weight of 12000 Da, to give a filtrate.

The filtrate was decolorized with 2 wt % activated carbon at 85° C. for 20 min, and filtered with a plate-and-frame filter to give a clear liquid, which was adjusted with sulfuric acid to pH 4.2 to carry out an acidification/crystallization, filtered and dried to give the DC12 crude product.

The DC12 crude product was purified by a high vacuum distillation, in which the rectifying column had a plate number of 24, an overhead pressure of 30 Pa, an overhead temperature of 240° C., a bottom temperature of 252° C., and a reflux ratio of 5:1. The fraction was collected and cooled to give the DC12 product.

Example 5-3. DC12, Microfiltration Membrane Filtration+Ultrafiltration Membrane Filtration+High Vacuum Distillation Following the fermentation method disclosed in Example 4 of CN1570124A, a dodecanedioic acid fermentation broth was obtained.

The DC12 fermentation broth was heated to 90° C., followed by adding a base to adjust the pH to 8.5. The fermentation broth was filtered at 90° C. with a ceramic microfiltration membrane having a pore size of 0.05 µm to remove the bacterial body, then cooled to 35° C., and filtered at 35° C. with an ultrafiltration membrane having a cut-off molecular weight of 5000 Da, to give a filtrate.

The filtrate was decolorized with 2 wt % activated carbon at 85° C. for 20 min, and filtered with a plate-and-frame filter to give a clear liquid, which was adjusted with sulfuric acid to pH 3 to carry out an acidification/crystallization, filtered and dried to give the DC12 crude product.

The DC12 crude product was purified by a high vacuum distillation, in which the rectifying column had a plate number of 24, an overhead pressure of 30 Pa, an overhead temperature of 240° C., a bottom temperature of 252° C., and a reflux ratio of 7:1. The fraction was collected and cooled to give the DC12 product.

Example 6-1. DC12, Microfiltration Membrane Filtration+Ultrafiltration Membrane Filtration+Melt Decolorization of Crude Product+High Vacuum Distillation Following the fermentation method disclosed in Example 4 of CN1570124A, a dodecanedioic acid fermentation broth was obtained.

The DC12 fermentation broth was heated to 90° C., followed by adding a base to adjust the pH to 8.5. The fermentation broth was filtered at 90° C. with a ceramic microfiltration membrane having a pore size of 0.25 µm to remove the bacterial body, then cooled to 35° C., and filtered at 35° C. with an ultrafiltration membrane having a cut-off molecular weight of 20000 Da, to give a filtrate. The filtrate was decolorized with 2 wt % activated carbon at 85° C. for 20 min, and filtered with a plate-and-frame filter to give a clear liquid.

The clear liquid was adjusted with sulfuric acid to pH 4.5 to carry out an acidification/crystallization, filtered and dried to give the DC12 crude product.

The DC12 crude product was heated and melted, and then decolorized with an activated carbon column composed of activated carbon particles at 150° C., in which the mass of the activated carbon particles was 40% of the mass of the DC12 crude product.

The decolorized DC12 crude product was purified by a high vacuum distillation, in which the rectifying column had a plate number of 20, an overhead pressure of 30 Pa, an overhead temperature of 230° C., a bottom temperature of 245° C., and a reflux ratio of 5:1. The fraction was collected and cooled to give the DC12 product.

Example 6-2. DC12, Microfiltration Membrane Filtration+Ultrafiltration Membrane Filtration+Melt Decolorization of Crude Product+High Vacuum Distillation Following the fermentation method disclosed in Example 4 of CN1570124A, a dodecanedioic acid fermentation broth was obtained.

The DC12 fermentation broth was heated to 90° C., followed by adding a base to adjust the pH to 8.5. The fermentation broth was filtered at 90° C. with a ceramic microfiltration membrane having a pore size of 0.15 μm to remove the bacterial body, then cooled to 35° C., and filtered at 35° C. with an ultrafiltration membrane having a cut-off molecular weight of 5000 Da, to give a filtrate. The filtrate was decolorized with 2 wt % activated carbon at 85° C. for 20 min, and filtered with a plate-and-frame filter to give a clear liquid.

The clear liquid was adjusted with sulfuric acid to pH 3 to carry out an acidification/crystallization, filtered and dried to give the DC12 crude product.

The DC12 crude product was heated and melted, and then decolorized with an activated carbon column composed of activated carbon particles at 150° C., in which the mass of the activated carbon particles was 40% of the mass of the DC12 crude product.

The decolorized DC12 crude product was purified by a high vacuum distillation, in which the rectifying column had a plate number of 22, an overhead pressure of 30 Pa, an overhead temperature of 230° C., a bottom temperature of 252° C., and a reflux ratio of 8:1. The fraction was collected and cooled to give the DC12 product.

Example 6-3. DC12, Microfiltration Membrane Filtration+Ultrafiltration Membrane Filtration+Melt Decolorization of Crude Product+High Vacuum Distillation Following the fermentation method disclosed in Example 4 of CN1570124A, a dodecanedioic acid fermentation broth was obtained.

The DC12 fermentation broth was heated to 90° C., followed by adding a base to adjust the pH to 8.5. The fermentation broth was filtered at 90° C. with a ceramic microfiltration membrane having a pore size of 0.05 μm to remove the bacterial body, then cooled to 35° C., and filtered at 35° C. with an ultrafiltration membrane having a cut-off molecular weight of 5000 Da, to give a filtrate. The filtrate was decolorized with 2 wt % activated carbon at 85° C. for 20 min, and filtered with a plate-and-frame filter to give a clear liquid.

The clear liquid was adjusted with sulfuric acid to pH 3 to carry out an acidification/crystallization, filtered and dried to give the DC12 crude product.

The DC12 crude product was heated and melted, and then decolorized with an activated carbon column composed of activated carbon particles at 140° C., in which the mass of the activated carbon particles was 25% of the mass of the DC12 crude product.

The decolorized DC12 crude product was purified by a high vacuum distillation, in which the rectifying column had a plate number of 18, an overhead pressure of 30 Pa, an overhead temperature of 240° C., a bottom temperature of 250° C., and a reflux ratio of 5:1. The fraction was collected and cooled to give the DC12 product.

Example 7. DC12, Microfiltration Membrane Filtration+Ultrafiltration Membrane Filtration+Melt Decolorization of Crude Product+Molecular Distillation Following the fermentation method disclosed in Example 4 of CN1570124A, a dodecanedioic acid fermentation broth was obtained.

The DC12 fermentation broth was heated to 90° C., followed by adding a base to adjust the pH to 8.5. The fermentation broth was filtered at 90° C. with a ceramic microfiltration membrane having a pore size of 0.05 μm to remove the bacterial body, then cooled to 35° C., and filtered at 35° C. with an ultrafiltration membrane having a cut-off molecular weight of 5000 Da, to give a filtrate.

The filtrate was decolorized with 2.5 wt % activated carbon at 85° C. for 20 min, and filtered with a plate-and-frame filter to give a clear liquid, which was adjusted with sulfuric acid to pH 3.0 to carry out an acidification/crystallization, filtered and dried to give the DC12 crude product.

The DC12 crude product was heated and melted, and then decolorized with an activated carbon column composed of activated carbon particles at 135° C., in which the mass of the activated carbon particles was 10% of the mass of the DC12 crude product.

The decolorized DC12 crude product was purified by a molecular distillation, in which the pressure in the main evaporator of the molecular distillation device was 3 Pa, the temperature of the evaporation surface of the main evaporator was 220° C., the temperature of the condensation surface of the main evaporator was 145° C., and the feedstock inlet temperature was 135° C. The fraction was collected and cooled to give the DC12 product.

Example 8. DC12, Microfiltration Membrane Filtration+Ultrafiltration Membrane Filtration+Melt Decolorization of Crude Product+Molecular Distillation Following the fermentation method disclosed in Example 4 of CN1570124A, a dodecanedioic acid fermentation broth was obtained.

The DC12 fermentation broth was heated to 90° C., followed by adding a base to adjust the pH to 8.5. The fermentation broth was filtered at 90° C. with a ceramic microfiltration membrane having a pore size of 0.05 μm to remove the bacterial body, then cooled to 35° C., and filtered at 35° C. with an ultrafiltration membrane having a cut-off molecular weight of 15000 Da, to give a filtrate.

The filtrate was decolorized with 2.5 wt % activated carbon at 85° C. for 20 min, and filtered with a plate-and-frame filter to give a clear liquid, which was adjusted with sulfuric acid to pH 4.2 to carry out an acidification/crystallization, filtered and dried to give the DC12 crude product.

The DC12 crude product was heated and melted, and then decolorized with an activated carbon column composed of activated carbon particles at 135° C., in which the mass of the activated carbon particles was 5% of the mass of the DC12 crude product.

The decolorized DC12 crude product was purified by a molecular distillation, in which the pressure in the main evaporator of the molecular distillation device was 16 Pa, the temperature of the evaporation surface of the main evaporator was 180° C., the temperature of the condensation surface of the main evaporator was 140° C., and the feedstock inlet temperature was 130° C. The fraction was collected and cooled to give the DC12 product.

Example 9. DC12, Microfiltration Membrane Filtration+Ultrafiltration Membrane Filtration+Molecular Distillation+Melt Decolorization of Fraction The present example and Example 4-1 were substantially the same in the starting materials used and the procedure, but were different in the following: the fraction obtained in the molecular distillation of Example 4-1 was further decolorized, in which the fraction obtained in the molecular distillation was heated and melted, and then decolorized with an activated carbon column composed of activated carbon particles at 135° C., in which the mass of the activated carbon particles was 15% of the mass of the DC12 crude product, and then cooled to give the DC12 product.

Comparative Example 1. DC12, Centrifugation+Dissolution by Base+Decolorization+Precipitation by Acid Following the fermentation method disclosed in Example 4 of CN1570124A, a dodecanedioic acid fermentation broth was obtained.

The DC12 fermentation broth was heated to 90° C., followed by adding a base to adjust the pH to 8.5. The fermentation broth was centrifuged to remove the bacterial body to give a clear liquid, which was adjusted with sulfuric acid to pH 3.0 to carry out an acidification/crystallization, filtered and dried to give the DC12 crude product.

To 100 g of the DC12 crude product was added 1000 g of water. The mixture was heated to 70° C., followed by adding caustic soda to adjust the pH to 10. The mixture was stirred so that dodecanedioic acid was completely dissolved. To the resulted solution was added 10 g of microporous powdered sugar charcoal. The mixture was stirred for 1 h and then filtered while hot to give a filtrate. To the filtrate was further added 10 g of microporous powdered sugar charcoal. The mixture was stirred for 1 h and then filtered while hot to give a filtrate. To the resulted filtrate was added sulfuric acid with a mass percentage concentration of 98% to adjust the pH to less than 3. The mixture was cooled to 25° C. and filtered to give the DC12 product.

Comparative Example 2. DC12, Centrifugation+Decolorization+Recrystallization from Ethyl Acetate Following the fermentation method disclosed in Example 4 of CN1570124A, a dodecanedioic acid fermentation broth was obtained.

The DC12 fermentation broth was heated to 90° C., followed by adding a base to adjust the pH to 8.5. The fermentation broth was centrifuged to remove the bacterial body. To the filtrate was added activated carbon in an amount of 2.5% of the mass of the filtrate for decolorization at 90° C. for 25 min. The mixture was filtered with a ceramic membrane at 90° C. to give a clear liquid, which was adjusted to pH 3.0 to carry out an acidification/crystallization, filtered and dried to give the DC12 crude product.

To 300 g of DC12 crude product was added 900 mL of ethyl acetate. The mixture was heated to 80° C. to dissolve the crude product. The mixture was filtered and kept at the same temperature for 60 min, then cooled to 25° C. to crystalize, and filtered. To the product obtained by the first crystallization was added 1000 mL of ethyl acetate. The mixture was heated to 80° C. to dissolve DC12. The mixture was kept at the same temperature for 30 min, then cooled to 25° C. in 1 h to crystalize, filtered and dried to give the DC12 product.

Comparative Example 3. DC16, Centrifugation+Dissolution by Base+Decolorization+Precipitation by Acid Following the fermentation method disclosed in Example 8 of CN1570124A, a hexadecandioic acid fermentation broth was obtained.

The fermentation broth was heated to 90° C., followed by adding a base to adjust the pH to 8.5. The fermentation broth was centrifuged to remove the bacterial body to give a clear liquid, which was adjusted with sulfuric acid to pH 3.0 to carry out an acidification/crystallization, filtered and dried to give the DC16 crude product.

To 100 g of the DC16 crude product was added 1500 g of water. The mixture was heated to 70° C., followed by adding caustic soda to adjust the pH to 10.2. The mixture was stirred so that hexadecandioic acid was completely dissolved. To the resulted solution was added 9.5 g of microporous powdered sugar charcoal. The mixture was stirred for 1 h and then filtered while hot to give a filtrate. To the filtrate was further added 10 g of microporous powdered sugar charcoal. The mixture was stirred for 1 h and then filtered while hot to give a filtrate. To the resulted filtrate was added sulfuric acid with a mass percentage concentration of 98% to adjust the pH to less than 3. The mixture was cooled to 25° C. and filtered to give the DC16 product.

The relative performances of the products obtained in the above examples and comparative examples were tested and the results are listed in Table 1.

TABLE 1

Performances of the long chain dicarboxylic acid products

| | Total acid content (%) | Purity(%) | Total N content (ppm) | Ash content (ppm) | Fe content (ppm) | Light Transmittance % | Residual solvent (ppm) | Yield % |
|---|---|---|---|---|---|---|---|---|
| Example 1. DC12 | 99.40% | 99.10% | 26 | 18 | 0.9 | 95% | Not detected | 95.5% |
| Example 2. DC12 | 99.42% | 99.27% | 22 | 16 | 0.8 | 96% | Not detected | 94.5% |
| Example 3. DC16 | 98.88% | 98.80% | 35 | 14 | 0.9 | 92% | Not detected | 95% |

TABLE 1-continued

Performances of the long chain dicarboxylic acid products

| | Total acid content (%) | Purity(%) | Total N content (ppm) | Ash content (ppm) | Fe content (ppm) | Light Transmittance % | Residual solvent (ppm) | Yield % |
|---|---|---|---|---|---|---|---|---|
| Example 4-1. DC12 | 99.69% | 99.60% | 20 | 10 | 0.8 | 97.5% | Not detected | 95% |
| Example 4-2. DC12 | 99.55% | 99.22% | 24 | 11 | 0.9 | 97% | Not detected | 95% |
| Example 4-3. DC12 | 99.50% | 99.18% | 24 | 13 | 0.9 | 96.4% | Not detected | 95% |
| Example 5-1. DC12 | 99.73% | 99.65% | 16 | 14 | 0.7 | 98.5% | Not detected | 94% |
| Example 5-2. DC12 | 99.70% | 99.60% | 18 | 15 | 0.8 | 98.4% | Not detected | 94% |
| Example 5-3. DC12 | 99.75% | 99.68% | 15 | 14 | 0.7 | 98.8 | Not detected | 94% |
| Example 6-1. DC12 | 99.80% | 99.70% | 14 | 10 | 0.8 | 99% | Not detected | 91.5% |
| Example 6-2. DC12 | 99.82% | 99.78% | 12 | 10 | 0.6 | 99.5% | Not detected | 91.5% |
| Example 6-3. DC12 | 99.80% | 99.75% | 15 | 11 | 0.7 | 99.1% | Not detected | 92% |
| Example 7. DC12 | 99.65% | 99.59% | 14 | 11 | 0.7 | 99.0% | Not detected | 92.6% |
| Example 8. DC12 | 99.60% | 99.54% | 15 | 11 | 0.8 | 98.6% | Not detected | 93.0% |
| Example 9. DC12 | 99.75% | 99.67% | 13 | 10 | 0.6 | 99.2% | Not detected | 92.5% |
| Comparative Example 1 | 98.50% | 98.01% | 170 | 890 | 3.5 | 90% | Not detected | 95% |
| Comparative Example 2 | 99.30% | 99.05% | 56 | 64 | 1.2 | 94% | 367 | 92% |
| Comparative Example 3 | 97.20% | 96.80% | 340 | 935 | 4.2 | 86% | Not detected | 96% |

Unless otherwise specified, all the terms used in the present disclosure have the meanings conventionally understood by a person skilled in the art.

The embodiments described in the present disclosure are for the purpose of illustration only, not for limiting the scope of the present disclosure. A person skilled in the art may make various substitutions, changes and modifications within the scope of the present disclosure. Therefore, the scope of the present disclosure is not limited to the above embodiments, but is defined by the appended claims.

The invention claimed is:

1. A method for refining a long chain dicarboxylic acid selected from $C_9$-$C_{18}$ dicarboxylic acids, comprising:
    (1) subjecting a long chain dicarboxylic acid fermentation broth or a treated liquid therefrom to membrane filtration, wherein the pH of the fermentation broth or the treated liquid is 6-12;
    (2) subjecting a filtrate from the membrane filtration to a decolorization treatment at a temperature of 50-100° C.;
    (3) subjecting the resulting filtrate to acidification/crystallization, solid-liquid separation, and drying to give a long chain dicarboxylic acid crude product; and
    (4) subjecting the long chain dicarboxylic acid crude product to vacuum distillation to give the long chain dicarboxylic acid product wherein the pressure in the vacuum distillation is ≤100 Pa;
    wherein the long chain dicarboxylic acid is a linear saturated dicarboxylic acid.

2. The method according to claim 1, wherein the membrane filtration comprises at least one of ultrafiltration membrane filtration and microfiltration membrane filtration.

3. The method according to claim 2, wherein a temperature for the microfiltration membrane filtration is 30-100° C. and a pore size of a microfiltration membrane is 0.01-1 μm.

4. The method according to claim 2, wherein a temperature for the ultrafiltration membrane filtration is 20-100° C. and a cut-off molecular weight of a ultrafiltration membrane is 1000-200000 Da.

5. The method according to claim 1, wherein the acidification/crystallization comprises adjusting the resulting filtrate to pH 2-4.5 for crystallization to occur.

6. The method according to claim 1, wherein the vacuum distillation is molecular distillation or high vacuum distillation.

7. The method according to claim 6, wherein a pressure in a main evaporator in the molecular distillation is 0.1-30 Pa; a temperature of an evaporation surface of the main evaporator is 130-250° C.; and a temperature of a condensation surface of the main evaporator is 130-160° C.

8. The method according to claim 6, wherein an overhead pressure of a rectifying column used in the vacuum distillation is 1-100 Pa and a bottom temperature of the rectifying column is 180-270° C.

9. The method according to claim 1, comprising: subjecting the long chain dicarboxylic acid crude product to a decolorization treatment before the vacuum distillation, or subjecting the long chain dicarboxylic acid product to a decolorization treatment after the vacuum distillation.

10. The method according to claim 9, wherein the decolorization treatment comprises a melt decolorization treatment, the melt decolorization treatment comprising heating and melting a solid to be decolorized and passing a melt form of the solid over a decolorant.

11. The method according to claim 10, wherein: a temperature for the decolorization treatment is 130-180° C.; the decolorant is activated carbon; and an amount of the activated carbon used in the melt decolorization treatment is 3-50% of the mass of the solid to be decolorized.

* * * * *